United States Patent [19]

Ikeda et al.

[11] Patent Number: 5,484,934
[45] Date of Patent: Jan. 16, 1996

[54] ISOTHIAZOLE DERIVATIVES, A PROCESS FOR PRODUCTION THEREOF AND USES THEREOF

[75] Inventors: Kenichi Ikeda, Kawanishi; Shin'ichi Ueyama, Urawa; Katsutoshi Endo; Chiaki Kato, both of Kawachinago, all of Japan

[73] Assignee: Nihon Nohyaku Co., Ltd., Tokyo, Japan

[21] Appl. No.: 174,063

[22] Filed: Dec. 18, 1993

[30] Foreign Application Priority Data

Dec. 30, 1992 [JP] Japan .................. 4-360826

[51] Int. Cl.⁶ .................. C07D 275/02; C07D 409/12; C07D 401/12
[52] U.S. Cl. .................. 548/213; 546/209
[58] Field of Search .................. 548/213; 546/209

[56] References Cited

U.S. PATENT DOCUMENTS 3,801,575  4/1974  Lewis et al. .................. 544/109
3,957,808  5/1976  Miller et al. .................. 548/213

FOREIGN PATENT DOCUMENTS 1555414  1/1969  France .
2050904  4/1972  Germany .

*Primary Examiner*—David B. Springer
*Attorney, Agent, or Firm*—Cushman Darby & Cushman

[57] ABSTRACT

An isothiazole derivative represented by the general formula (I):

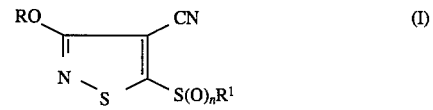

(wherein R and $R^1$ are as defined in the general description, and n is an integer of 1 or 2), a process for producing the same, and the usage thereof.

5 Claims, No Drawings

ISOTHIAZOLE DERIVATIVES, A PROCESS FOR PRODUCTION THEREOF AND USES THEREOF

BACKGROUND OF THE INVENTION

1. Field of the Invention

The present invention relates to isothiazole derivatives represented by the general formula (I):

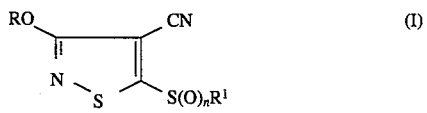

[wherein R is a hydrogen atom; a $C_{1-12}$ alkyl group; a $C_{2-7}$ alkenyl group; a $C_{3-7}$ alkynyl group; a $C_{3-7}$ cycloalkyl group; a substituted alkyl group having as the substituent(s) 1 or 2 atoms or groups selected from the group consisting of halogen atoms, $C_{1-6}$ alkoxy groups, cyano group, $C_{2-7}$ alkoxycarbonyl groups, phenyl group, phenoxy group, phenoxyphenyl group, heteroaryl groups, trialkylsilyl groups, $C_{2-7}$ alkylcarbonyl groups, and groups represented by the formula —A—N($R^2$)$_2$ (wherein $R^2$ is a $C_{1-6}$ alkyl group or forms a $C_{2-6}$ alkylene group by binding of two $R^2$'s to each other, and A is a carbonyl group or a $C_{2-6}$ alkylene group); or a substituted $C_{2-7}$ alkenyl group having a halogen atom or a phenyl group as the substituent, $R_1$ is a $C_{1-12}$ alkyl group; a $C_{2-7}$ alkenyl group; a $C_{3-7}$ alkynyl group; a $C_{3-7}$ cycloalkyl group; a heteroarylalkyl group; a substituted $C_{1-6}$ alkyl group having as the substituent a group selected from the group consisting of phenyl group, substituted phenoxy groups having 1 or 2 halogen atoms as the substituent(s), and phenoxyphenyl group; or an aryl group, $R^1$ being an aryl group in the case of R being a hydrogen atom, and n is an integer of 1 or 2], a process for production of said derivatives, and wood preservatives and agricultural and horticultural fungicides, which are characterized by containing said derivative as an active ingredient.

2. Related Art

The compounds of the general formula (I) are novel compounds which have not been known in any literature. As to isothiazole derivatives, French Patent No. 1,555,414 discloses the fungicidal activity of 3-hydroxy-4-cyano-5-alkylsulfonylisothiazoles and a production process of these compounds using perbenzoic acid but does not describe the compounds as having preservative activity for wood.

SUMMARY OF THE INVENTION

The present invention is intended to provide a wood preservative and an agricultural and horticultural fungicide.

The present inventors investigated isothiazole derivatives and consequently found that the compounds of the above general formula (I) have excellent preservative activity for wood and fungicidal activity for agricultural and horticultural use, whereby the present invention has been accomplished.

DETAILED DESCRIPTION OF THE PREFERRED EMBODIMENTS

The present invention relates to isothiazole derivatives represented by the general formula (I):

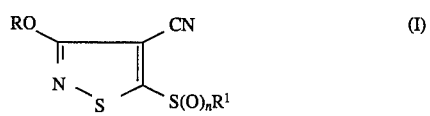

[wherein R is a hydrogen atom; a $C_{1-12}$ alkyl group; a $C_{2-7}$ alkenyl group; a $C_{3-7}$ alkynyl group; a $C_{3-7}$ cycloalkyl group; a substituted alkyl group having as the substituent(s) 1 or 2 atoms or groups selected from the group consisting of halogen atoms, $C_{1-6}$ alkoxy groups, cyano group, $C_{2-7}$ alkoxycarbonyl groups, phenyl group, phenoxy group, phenoxyphenyl group, heteroaryl groups, trialkylsilyl groups, $C_{2-7}$ alkylcarbonyl groups, and groups represented by the formula —A—N($R^2$)$_2$ (wherein $R^2$ is a $C_{1-6}$ alkyl group or forms a $C_{2-6}$ alkylene group by binding of two $R^2$'s to each other, and A is a carbonyl group or a $C_{2-6}$ alkylene group); or a substituted $C_{2-7}$ alkenyl group having a halogen atom or a phenyl group as the substituent, $R_1$ is a $C_{1-12}$ alkyl group; a $C_{2-7}$ alkenyl group; a $C_{3-7}$ alkynyl group; a $C_{3-7}$ cycloalkyl group; a heteroarylalkyl group; a substituted $C_{1-6}$ alkyl group having as the substituent a group selected from the group consisting of phenyl group, substituted phenoxy groups having 1 or 2 halogen atoms as the substituent(s), and phenoxyphenyl group; or an aryl group, $R^1$ being an aryl group in the case of R being a hydrogen atom, and n is an integer of 1 or 2], a process for production of said derivatives, and wood preservatives and agricultural and horticultural fungicides, which are characterized by containing said derivative as an active ingredient.

In the definition of R and $R^1$ in the above general formula (I), the $C_{1-12}$ alkyl group includes linear or branched alkyl groups such as methyl, ethyl, isopropyl, n-propyl, n-butyl, isobutyl, sec-butyl, tert-butyl, n-pentyl, n-hexyl, n-dodecyl, n-octadecyl, etc.; the $C_{2-7}$ alkenyl group includes vinyl group, 1-propenyl group, 2-propenyl group, 1-methyl-2-propenyl group, 1,1-dimethyl- 2-propenyl group, butenyl group, pentenyl group, hexenyl group, etc.; the $C_{3-7}$ alkynyl group includes 2-propynyl group, 1-methyl-2-propynyl group, 1,1-dimethyl-2-propynyl group, butynyl group, pentynyl group, hexynyl group, etc.; the cycloalkyl group includes cyclopropyl group, cyclopentyl group, cyclohexyl group, etc.; the haloalkenyl group includes 3-chloropropenyl group, 2-chloropropenyl group, etc.; the substituted alkyl group includes those having substituent(s) selected from the group consisting of, for example, $C_{1-6}$ alkoxy groups such as methoxy, ethoxy, n-propoxy, n-butoxy, t-butoxy, etc., alkoxycarbonyl groups such as methoxycarbonyl, ethoxycarbonyl, n-propoxycarbonyl, isopropoxycarbonyl, etc., $C_{2-7}$ alkylcarbonyl groups such as methylcarbonyl, ethylcarbonyl, n-propylcarbonyl, isopropylcarbonyl, etc., $C_{2-12}$ dialkylamino groups such as dimethylamino, diethylamino, diisopropylamino, etc., $C_{3-13}$ dialkylaminocarbonyl groups such as dimethylaminocarbonyl, diethylaminocarbonyl, diisopropylaminocarbonyl, etc., cyanocarbinyl group, trialkylsilyl groups such as trimethylsilyl, triethylsilyl, etc., phenyl group, substituted aryl groups having a p-tolyl group, a t-butylphenyl group or the like as the substituent, cyano group, 2,4-dichlorophenoxy group, and heteroaromatic groups such as 1,2,4-triazol-2-yl group, benzimidazole group, 3,5-dimethyloxazol-4-yl group, 2-chloropyrid- 5-yl group, etc.

In the definition of $R_1$, the aryl group includes substituted phenyl groups having as the substituent(s) 1 to 3 atoms or groups selected from the group consisting of $C_{1-6}$ alkyl groups, fluorine atom, chlorine atom, bromine atom, nitro group, amino group, hydroxyl group, carboxyl group, alkoxycarbonyl groups, alkoxy groups, phenoxy groups, trifluoromethyl group, etc.

The compound of the general formula (I) can be synthesized by the following method.

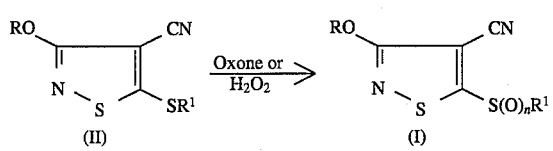

wherein R, R¹ and n are as defined above.

That is, the isothiazole derivative of the general formula (I) can be obtained by reacting a compound of the general formula (II) with potassium peroxymonosulfate (Oxone) or hydrogen peroxide.

In the reaction, any solvent may be used so long as it does not inhibit the reaction. There may be used, for example, alcohols such as methanol, ethanol, isopropanol, t-butanol, diethylene glycol, etc.; ketones such as acetone, methyl ethyl ketone, cyclohexanone, etc.; nitriles such as acetonitrile, etc.; water-soluble solvents such as acetic acid, tetrahydrofuran, dimethylformamide, dimethyl sulfoxide, etc.; and mixed solvents of the alcohols, the ketones or the nitriles and the water-soluble solvents. When two-phase reaction is carried out as the above reaction by using the mixed solvent, there can be used phase transfer catalysts such as triethylbenzylammonium chloride, trioctylmethylammonium chloride, etc.

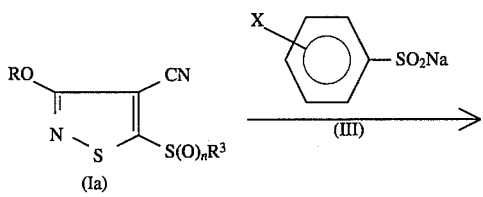

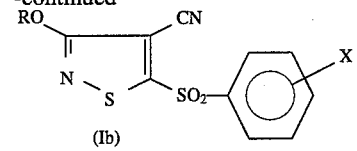

wherein R and n are as defined above, $R^3$ is a $C_{1-6}$ alkyl group, and X is a halogen atom, a $C_{1-6}$ alkyl group, a $C_{1-6}$ alkoxy group, a hydroxyl group, a nitro group, an amino group or a $C_{2-7}$ alkoxycarbonyl group.

That is, an isothiazole derivative of the general formula (Ib) can be obtained by reacting a compound of the general formula (Ia) with an arylsulfinic acid salt of the general formula (III).

In this reaction, any solvent may be used so long as it does not inhibit the reaction. There may be used, for example, alcohols such as methanol, ethanol, isopropanol, t-butanol, diethylene glycol, etc.; ketones such as acetone, methyl ethyl ketone, cyclohexanone, etc.; ethers such as diethyl ether, diisopropyl ether, dimethoxyethane, tetrahydrofuran, dioxane, monoglyme, diglyme, etc.; esters such as methyl acetate, ethyl acetate, etc.; halogenated hydrocarbons such as dichloroethane, chloroform, carbon tetrachloride, tetrachloroethane, etc.; aromatic hydrocarbons such as benzene, chlorobenzene, nitrobenzene, toluene, etc.; nitriles such as acetonitrile, etc.; dimethylformamide; dimethyl sulfoxide; water; and mixed solvents obtained by combining solvents selected from the above solvents. When two-phase reaction is carried out as the above reaction by the use of the mixed solvent, there can be used phase transfer catalysts such as triethylbenzylammonium chloride, trioctylmethylammonium chloride, etc.

The reaction temperature is properly chosen in the range of 0° C. to 100° C. It is preferably 40° C. to 60° C. Although the reaction time is varied depending on the reaction temperature and the degree of reaction, it is usually chosen in the range of 30 minutes to 12 hours.

Since the reaction is an equimolar reaction, it is sufficient that the reactants are used in equimolar amounts, though either of them may be used in excess.

Examples of the compound of the general formula (I) are given in Table 1 but they are not intended in any way to limit the scope of the present invention.

TABLE 1

| No. | R | n | R¹ | Physical property (m.p. °C.) |
|---|---|---|---|---|
| 1 | H | 2 | phenyl | 163–164 |
| 2 | " | " | 4-CH₃-phenyl | 142–144 |
| 3 | " | " | 4-C₄H₉-t-phenyl | 117–120 |

TABLE 1-continued $$\underset{\underset{S}{N}}{\overset{RO}{\bigg|}}\!\!\!\!\!\!\!\!\!\!\!\!\!\!\!\!\!\!\!\!\!\!\!\!\!\overset{CN}{\underset{S(O)_nR^1}{\bigg|}}$$

| No. | R | n | R$^1$ | Physical property (m.p. °C.) |
|---|---|---|---|---|
| 4 | " | " | 4-Cl-C$_6$H$_4$ | 197–198 |
| 5 | " | " | 2-(CO$_2$C$_2$H$_5$)-C$_6$H$_4$ | 151–152 |
| 6 | " | " | 2-CH$_3$-4-Cl-C$_6$H$_3$ | 161–163 |
| 7 | " | " | 4-OCH$_3$-C$_6$H$_4$ | 146–147 |
| 8 | " | " | 3-Cl-C$_6$H$_4$ | 171–172 |
| 9 | " | " | 2-Cl-C$_6$H$_4$ | 165–166 |
| 10 | " | " | 3-CH$_3$-C$_6$H$_4$ | 136–137 |
| 11 | " | " | 4-F-C$_6$H$_4$ | 154–156 |
| 12 | H | 2 | 4-OH-C$_6$H$_4$ | 171–172 |
| 13 | " | " | 4-NO$_2$-C$_6$H$_4$ | 231–233 |

TABLE 1-continued $$\begin{array}{c} RO \quad CN \\ \diagdown \quad \diagup \\ N \diagdown_S \diagup S(O)_n R^1 \end{array}$$

| No. | R | n | R¹ | Physical property (m.p. °C.) |
|---|---|---|---|---|
| 14 | " | " | 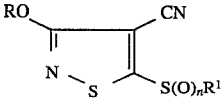 3-NH$_2$-phenyl | 191–192 |
| 15 | CH$_3$ | 1 | CH$_3$ | 123–124 |
| 16 | CH≡C—CH$_2$— | " | " | 48–50 |
| 17 | CH$_2$=C(CH$_3$)—CH$_2$— | " | " | 107–108 |
| 18 | CH$_3$ | " | —CH$_2$CO$_2$C$_2$H$_5$ | 71–72 |
| 19 | n-C$_{12}$H$_{25}$— | " | CH$_3$ | 65–67 |
| 20 | CH$_3$ | 2 | CH$_3$ | 167–168 |
| 21 | C$_2$H$_5$ | " | " | 134–135 |
| 22 | CH$_2$=CH—CH$_2$— | " | " | 75–76 |
| 23 | C$_2$H$_5$ | " | C$_2$H$_5$ | 86–87 |
| 24 | F$_2$CH | " | CH$_3$ | 108–109 |
| 25 | " | " | C$_2$H$_5$ | 58–59 |
| 26 | " | " | n-C$_3$H$_7$ | 71–72 |
| 27 | " | " | i-C$_3$H$_7$ | 85.8 |
| 28 | " | " | s-C$_4$H$_9$ | 42–43 |
| 29 | F$_2$CH | 2 | t-C$_4$H$_9$ | 89–90 |
| 30 | " | " | 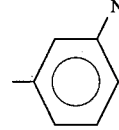 cyclopentyl | 63–64 |
| 31 | " | " |  cyclohexyl | 81–82 |
| 32 | " | " |  PhCH$_2$— | 101–102 |
| 33 | " | " | (C$_2$H$_5$)$_2$CH— | 73–74 |
| 34 | " | " | S-C$_5$H$_{11}$ | 67–68 |
| 35 | CH$_3$ | " | i-C$_3$H$_7$ | 57 |
| 36 | " | " | n-C$_4$H$_9$ | 51–52 |
| 37 | " | " | C$_2$H$_5$ | 106.9 |
| 38 | C$_2$H$_5$ | " | i-C$_3$H$_7$ | 78–79 |
| 39 | " | " | n-C$_4$H$_9$ | 56–57 |
| 40 | " | " | n-C$_6$H$_{13}$— | 54–55 |
| 41 | " | " | n-C$_8$H$_{17}$ | 49–50 |
| 42 | " | " | CH$_3$O$_2$C—CH$_2$— | 69–70 |
| 43 | n-C$_3$H$_7$ | " | CH$_3$ | 97–98 |
| 44 | " | " | C$_2$H$_5$ | 78–79 |
| 45 | " | " | n-C$_3$H$_7$ | 54–55 |
| 46 | " | " | i-C$_3$H$_7$ | 81–82 |
| 47 | " | " | n-C$_4$H$_9$ | 74–75 |
| 48 | " | " | n-C$_6$H$_{13}$ | 61–62 |
| 49 | " | " | 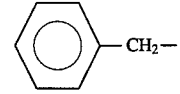 PhCH$_2$— | 68–69 |

TABLE 1-continued structure: isothiazole with RO at 3-position, CN at 4-position, S(O)ₙR¹ at 5-position

| No. | R | n | R¹ | Physical property (m.p. °C.) |
|---|---|---|---|---|
| 50 | i-C$_3$H$_7$ | 2 | CH$_3$ | 97.1 |
| 51 | " | " | i-C$_3$H$_7$ | 98–99 |
| 52 | " | " | n-C$_4$H$_9$ | 83–84 |
| 53 | " | " | n-C$_6$H$_{13}$ | 64–65 |
| 54 | n-C$_4$H$_9$ | " | CH$_3$ | 74–75 |
| 55 | " | " | C$_6$H$_5$–CH$_2$– | 125.7 |
| 56 | CH$_2$=CH–CH$_2$– | " | i-C$_3$H$_7$ | 57–58 |
| 57 | CH$_3$–CH=CH–CH$_2$– | " | CH$_3$ | 107–109 |
| 58 | CH≡C–CH$_2$– | " | C$_2$H$_5$ | 97.5 |
| 59 | ClCH=CH–CH$_2$– | " | " | 59–60 |
| 60 | CH$_2$=C(Cl)–CH$_2$– | " | " | 61–62 |
| 61 | CH$_2$=CH–CH$_2$– | " | C$_6$H$_5$– | 157.6 |
| 62 | CH$_2$=C(CH$_3$)–CH$_2$– | " | C$_6$H$_5$– | 105–106 |
| 63 | C$_2$H$_5$O$_2$C–CH$_2$– | " | i-C$_3$H$_7$ | 60–61 |
| 64 | (CH$_3$)$_3$C–C(O)–CH$_2$– | " | CH$_3$ | 83–84 |
| 65 | n-C$_5$H$_{11}$ | " | " | 91–92 |
| 66 | cyclopentyl | " | " | 101–102 |
| 67 | n-C$_6$H$_{13}$ | " | " | 90–91 |
| 68 | n-C$_8$H$_{17}$ | " | " | 80–81 |
| 69 | n-C$_{10}$H$_{21}$ | 2 | CH$_3$ | 82–83 |
| 70 | n-C$_{12}$H$_{25}$ | 1 | " | 65–66 |
| 71 | " | 2 | " | 72–73 |
| 72 | cyclohexyl | " | " | 132–133 |
| 73 | C$_2$H$_5$OCH$_2$CH$_2$– | " | " | 70–71 |
| 74 | C$_6$H$_5$–CH$_2$CH$_2$– | " | " | 112–113 |
| 75 | NCCH$_2$– | " | " | 126–127 |
| 76 | C$_6$H$_5$–CH$_2$– | " | C$_6$H$_5$–CH$_2$– | 134.8 |

TABLE 1-continued

Structure:
$$\text{RO} - \text{C} = \text{C(CN)} - \text{C(S(O)}_n\text{R}^1\text{)} = \text{N} - \text{S (isothiazole ring)}$$

| No. | R | n | R¹ | Physical property (m.p. °C.) |
|---|---|---|---|---|
| 77 | (CH₃)₃SiCH₂— | " | i-C₃H₇ | 98–99 |
| 78 | C₆H₅—OCH₂CH₂— | " | CH₃ | 106–107 |
| 79 | CH₃C(O)CH₂— | " | C₂H₅ | 91–92 |
| 80 | CH₃ | " | 2,4-Cl₂C₆H₃—OCH₂CH₂— | 134–135 |
| 81 | " | " | CH₃O₂C—CH₂— | 75–76 |
| 82 | CH≡C—CH₂— | " | C₂H₅OCH₂CH₂— | 66–67 |
| 83 | i-C₃H₇ | " | C₆H₅—O—C₆H₄—CH₂— | 91–92 |
| 84 | C₆H₅—CH=CH—CH₂— | " | CH₃ | 114–115 |
| 85 | (CH₃)₂NC(O)—CH₂— | " | " | 141–143 |
| 86 | piperidino—CH₂CH₂— | 2 | CH₃ | 112–114 |
| 87 | (C₆H₅)₂CH— | " | " | 88–89 |
| 88 | C₆H₅—O—C₆H₄—CH₂— | " | " | 91–92 |
| 89 | CH₃ | " | C₆H₅— | 63–64 |
| 90 | " | " | 4-CH₃—C₆H₄— | 108–109 |

TABLE 1-continued
$$\underset{N\diagdown S}{RO}\diagup\underset{S(O)_nR^1}{CN}$$
| No. | R | n | R¹ | Physical property (m.p. °C.) |
|---|---|---|---|---|
| 91 | " | " | 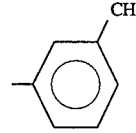 3-CH₃-C₆H₄ | 80–81 |
| 92 | " | " | 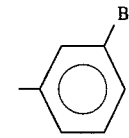 3-Br-C₆H₄ | 109–110 |
| 93 | " | " | 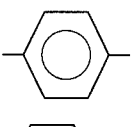 4-Cl-C₆H₄ | 120–121 |
| 94 | " | " | 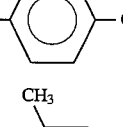 4-OCH₃-C₆H₄ | 119–120 |
| 95 | " | " | 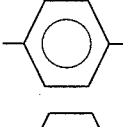 2-CH₃-4-Cl-C₆H₃ | 106–108 |
| 96 | " | " | 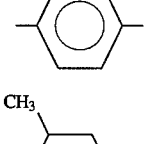 4-F-C₆H₄ | 101–102 |
| 97 | " | " | 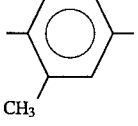 2,4,6-(CH₃)₃-C₆H₂ | 111–113 |
| 98 | C₂H₅ | " | 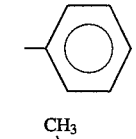 C₆H₅ | 84.7 |
| 99 | C₂H₅ | 2 | 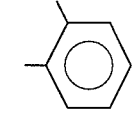 2-CH₃-C₆H₄ | 107–108 |
| 100 | " | " | 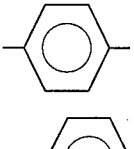 4-Cl-C₆H₄ | 92–93 |
| 101 | n-C₃H₇ | " | 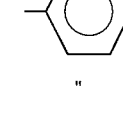 C₆H₅ | 72–73 |
| 102 | i-C₃H₇ | " | " | 96–97 |

TABLE 1-continued
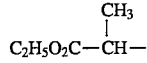
| No. | R | n | R$^1$ | Physical property (m.p. °C.) |
|---|---|---|---|---|
| 103 | CH$_2$=CH—CH$_2$— | " | " | 72–73 |
| 104 | CH≡C—CH$_2$— | " | " | 118–119 |
| 105 | n-C$_4$H$_9$ | " | " | 62–63 |
| 106 | F$_2$CH— | " | " | 65–66 |
| 107 | C$_2$H$_5$OCH$_2$CH$_2$— | " | " | 63–64 |
| 108 | C$_2$H$_5$O$_2$C—CH(CH$_3$)— | " | " | 94–95 |
| 109 | CH$_3$O$_2$C—CH$_2$— | " | " | 103–104 |
| 110 | F$_2$CH— | " | 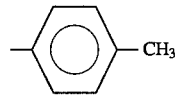 4-CH$_3$-C$_6$H$_4$— | 115–116 |
| 111 | " | " |  4-Cl-C$_6$H$_4$— | 137–138 |
| 112 | " | " | 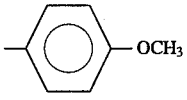 4-OCH$_3$-C$_6$H$_4$— | 114–115 |
| 113 | " | " | 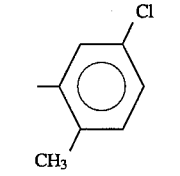 2-CH$_3$-4-Cl-C$_6$H$_3$— | 93–94 |
| 114 | " | " | 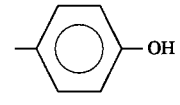 4-OH-C$_6$H$_4$— | 110–111 |
| 115 | F$_2$CH— | 2 | 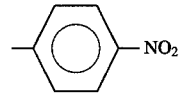 4-NO$_2$-C$_6$H$_4$— | 161–163 |
| 116 | " | " | 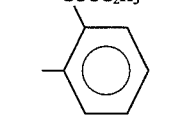 2-COOC$_2$H$_5$-C$_6$H$_4$— | 131–132 |
| 117 | " | " | 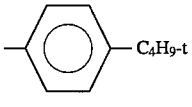 4-t-C$_4$H$_9$-C$_6$H$_4$— | 62–63 |
| 118 | " | " | 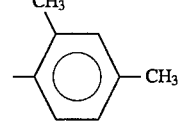 2,4-(CH$_3$)$_2$-C$_6$H$_3$— | 91–92 |

TABLE 1-continued $$\underset{N\diagdown S}{\overset{RO}{\underset{}{\bigg|}}}\overset{CN}{\underset{S(O)_nR^1}{\bigg|}}$$

| No. | R | n | R¹ | Physical property (m.p. °C.) |
|---|---|---|---|---|
| 119 | $CH_2=CH-CH_2-$ | " | 4-CH₃-C₆H₄- | 67–68 |
| 120 | $HC\equiv C-CH_2-$ | " | 4-Cl-C₆H₄- | 98–99 |
| 121 | $Cl-CH=CH-CH_2-$ | " | 4-CH₃-C₆H₄- | 56–57 |
| 122 | $CH_3O_2CCH_2-$ | " | 4-F-C₆H₄- | 117–118 |
| 123 | $(CH_2)_3Si-CH_2-$ | " | 3-Cl-C₆H₄- | 91–92 |
| 124 | $CH_3\overset{O}{\underset{}{\overset{\|}{C}}}CH_2-$ | " | 2-Cl-C₆H₄- | 103–104 |
| 125 | $C_2H_5OCH_2CH_2-$ | " | 2-CH₃-C₆H₄- | 111–113 |
| 126 | $n\text{-}C_4H_9$ | " | 4-OCH₃-C₆H₄- | 74–75 |
| 127 | cyclopentyl | " | 4-CH₃-C₆H₄- | 90–92 |
| 128 | cyclohexyl | 2 | 4-CH₃-C₆H₄- | 101–102 |
| 129 | $C_6H_5CH_2-$ | " | 4-Cl-C₆H₄- | 121–123 |
| 130 | $n\text{-}C_8H_{17}$ | " | C₆H₅- | 81–82 |

TABLE 1-continued $$\underset{N\diagdown S}{\overset{RO}{\underset{\|}{\bigwedge}}}\overset{CN}{\underset{S(O)_nR^1}{}}$$

| No. | R | n | R¹ | Physical property (m.p. °C.) |
|---|---|---|---|---|
| 131 | ![pyrazolyl-CH₂-] N=N-CH₂- (imidazole) | " | CH₃ | 224–225 |
| 132 | Cl-pyridyl-CH₂- | " | C₂H₅ | 182–183 |
| 133 | C₆H₅-CH=CH-CH₂- | " | CH₃ | 132–133 |
| 134 | CH₃ | " | —CH₂CH=CH₂ | 86–87 |
| 135 | " | " | —CH₂CH=CHCl | 83–84 |
| 136 | " | " | —CH₂C≡CH | 91–92 |
| 137 | " | " | —CH₂—N—N (imidazolyl) | 164–165 |
| 138 | " | " | —CH₂-benzimidazol-2-yl (NH) | 250 (decomp.) |
| 138 | " | " | —CH₂-(4-methyl-1,2-oxazol-3-yl with CH₃) | 123–125 |
| 140 | CH₃ | " | CHF₂ | 83–84 |
| 141 | C₂H₅ | " | " | 61–62 |
| 143 | n-C₃H₇ | 2 | CHF₂ | 56–57 |
| 144 | i-C₃H₇ | " | " | 60–61 |
| 145 | s-C₄H₉ | " | " | 51–53 |
| 146 | s-C₅H₁₁ | " | " | 60–62 |
| 147 | CH₂=CH—CH₂— | " | " | 48–49 |
| 148 | CH≡C—CH₂— | " | " | 52–53 |
| 149 | cyclopentyl | " | " | 71–72 |
| 150 | C₂H₅OCH₂CH₂— | " | " | 68–69 |

EXAMPLES

Examples of the present invention are described below but should not be construed as limiting the scope of the invention.

Example 1

Synthesis of 3-hydroxy-4-cyano-5-methylsulfonylisothiazole

With 1.72 g (0.01 mole) of 3-hydroxy- 4-cyano5-methylthio-1, 2-thiazole was mixed 1.54 g (0.025 mole of Oxone (2KHSO₅.KHSO₄.K₂SO₄), and 20 ml of water was added. With stirring, 4 ml of concentrated sulfuric acid was added dropwise, and the stirring was continued for 15 hours. Water was added to the reaction mixture and the crystals precipitated were collected by filtration and washed with water. The crystals were washed with ethyl acetate and recrystallized from acetone to obtain 1.5 g (yield 79%) of white crystals having a melting point (decomposition) of 225° C.

Example 2

Synthesis of 3-hydroxy-4-cyano-5-benzylsulfonylisothiazole

In 30 ml of water was suspended 2.48 g (0.01 mole) of 3-hydroxy-4-cyano-5-benzylthioisothiazole, and 10 g (0.016 mole) of Oxone was added and then stirred for 2 days. Water was added to the reaction mixture and the crystals precipitated were collected by filtration, washed with water, dried and then recrystallized from ethyl acetate to obtain 2.4 g (yield 85%) of white crystals having a melting point of 181–183° C.

$^1$HNMR (CDCl$_3$) σ; 4.58 (2H, s), 7.25–7.40 (5H, m)

Example 3

Synthesis of 3-methoxy-4-cyano-5-methylsulfonylisothiazole

At room temperature, 1.86 g (0.01 mole) of 3-methoxy-4-cyano-5-methylthioisothiazole was stirred together with 5 ml of ethanol, 18 g (0.029 mole) of Oxone and 20 ml of water. Then, 1 ml of concentrated sulfuric acid was added dropwise and stirred for 5 hours. Water was added and the crystals precipitated were collected by filtration, washed with water, dried and then recrystallized from ethyl acetate to obtain 1.7 g (yield 78%) of white crystals having a melting point of 167–168° C.

$^1$HNMR (CDCl$_3$) σ; 3.34 (3H, s), 4.14 (3H, s)

Example 4

Synthesis of 3-difluoromethoxy-4-cyano-5-methylsulfonyl-isothiazole

At room temperature, 2.22 g (0.01 mole) of 3-difluoromethoxy- 4-cyano-5-methylthioisothiazole was stirred together with 5 ml of tetrahydrofuran, 12.8 g (0.021 mole) of Oxone and 15 ml of water. Thereafter, 3 ml of 50% sulfuric acid was added and then stirred for 6 hours. Water was added and the desired compound was extracted with ethyl acetate, washed with water and then dried. The ethyl acetate was distilled off under reduced pressure to obtain 2.5 g of crude crystals. The crude crystals were recrystallized from ethyl acetate to obtain white crystals having a melting point of 109° C.

$^1$HNMR (CDCl$_3$) σ;3.40 (3H, s), 6.90–7.60 (1H, t, J=6.8 Hz)

Example 5

Synthesis of 3-trimethylsilylmethoxy-4-cyano-5-isopropyl-sulfonylisothiazole

In 10 ml of acetic acid was dissolved 2.86 g (0.01 mole) of 3-trimethylsilylmethoxy-4-cyano-5-isopropylthioisothiazole, followed by adding thereto 15 ml of water and then 15 g (0.025 mole) of Oxone. The resulting mixture was stirred at room temperature for 10 hours. Water was added and the desired compound was extracted with ethyl acetate, washed with water and then dried. The ethyl acetate was distilled off under reduced pressure to obtain 3.1 g of crude crystals. The crude crystals were recrystallized from ether to obtain white crystals having a melting point of 98–99° C.

$^1$HNMR (CDCl$_3$) σ;0.00 (9H, s), 1.30 (6H, d), 3.30–3.40 (1H, m), 4.00 ( 2H, s)

Example 6

Synthesis of 3-hydroxy-4-cyano-5-phenylsulfonylisothiazole

In 20 ml of water was suspended 2.35 g (0.01 mole) of 3-hydroxy-4-cyano-5-phenylthioisothiazole, followed by adding thereto 15 g (0.025 mole) of Oxone and then 10 ml of dimethoxyethane. The resulting mixture was stirred for 24 hours. Water was added to the reaction mixture and the crystals precipitated were collected by filtration, washed with water, and then dried to obtain 2.4 g of crude crystals. The crude crystals were recrystallized from ethyl acetate to obtain 2.2 g (yield 84%) of crystals having a melting point of 163–164° C.

Example 7

Synthesis of 3-methoxy-4-cyano-5-(4-methylphenyl) sulfonylisothiazole

In 15 ml of ethyl acetate was dissolved 2.18 g (0.01 mole) of 3-methoxy-4-cyano-5-methylsulfonylisothiazole, and a solution of 2.0 g (0.011 mole) of sodium p-tolylsulfinate in 15 ml of water was added with stirring at room temperature. The resulting mixture was stirred with heating at 60° C. for 30 minutes. To the mixture were added 20 ml of ethyl acetate and then 50 ml of water, and the resulting mixture was well shaken to separate an ethyl acetate layer. The ethyl acetate layer was washed with water and dried, after which the ethyl acetate was distilled off under reduced pressure to obtain 2.5 g of crude crystals. The crude crystals were recrystallized from isopropyl ether to obtain 1.5 g of white crystals having a melting point of 109° C.

$^1$HNMR (CDCl$_3$) σ; 2.46 (3H, s), 4.06 (3H, s), 7.41–7.43 (2H, d), 7.99–8.02 (2H, d)

Example 8

Synthesis of 3-propargyloxy-4-cyano-5-methysulfonyl-isothiazole

In 10 ml of acetic acid was suspended 2.1 g (0.01 mole) of 3-propargyloxy-4-cyano-5-methylthioisothiazole, followed by adding thereto 3.5 g (0.0057 mole) of Oxone and then 10 ml of water. The resulting mixture was stirred for 24 hours. Water was added to the reaction mixture and the desired compound was extracted with ethyl acetate. The extract was washed with water, dried and then concentrated under reduced pressure to obtain 2.1 g of crude crystals. The crude crystals were purified by a silica gel column chromatography to remove the unreacted starting materials, whereby 1.6 g (yield 66%) of crystals having a melting point of 48–50° C. was obtained.

$^1$HNMR (CDCl$_3$) σ;2.55–2.65 (1H, m), 3.10 (3H, s), 5.03–5.13 (2H, d),

Example 9

Synthesis of 3-methoxy-4-cyano-5-methylsulfoxyisothiazole

After 1.86 g (0.01 mole) of 3-methoxy-4-cyano- 5-methylthioisothiazole was sufficiently ground, and 10 ml of ethanol, 4 g (0.0065 mole) of Oxone and 10 ml of water were added. With stirring, 1 ml of concentrated sulfuric acid was added dropwise, and the stirring was continued for 8 hours. Water was added to the reaction mixture and the crystals precipitated were collected by filtration, washed with water, dried and then subjected to fractional recrystallization to obtain 1.2 g (yield 59%) of white crystals having a melting point of 124° C.

$^1$HNMR (CDCl13) σ; 3.10 (3H, s), 4.14 (3H, s),

Example 10

Synthesis of 3-methoxy-4-cyano-5-phenylsulfonylisothiazole

In 10 ml of ethyl acetate was dissolved 1.2 g (0.0059 mole) of 3-methoxy-4-cyano-5-methylsulfoxyisothiazole, followed by adding thereto a solution of 1.2 g (0.007 mole) of sodium benzenesulfinate in 10 ml of water, and the reaction was carried out with heating under reflux for 1 hour.

Water was added to the reaction mixture and the desired compound was extracted with ethyl acetate, washed with water, and then dried. Thereafter, the ethyl acetate was distilled off under reduced pressure to obtain 1.5 g of crude crystals. The crude crystals were recrystallized from ethyl acetate to obtain 1.0 g (yield 60%) of white crystals having a melting point of 64° C.

Example 11

Synthesis of 3-difluoromethoxy-4-cyano-5-cyclopentylsulfonylisothiazole

In 10 ml of acetic acid was dissolved 2.76 g (0.01 mole) of 3-difluoromethoxy-4-cyano-5-cyclopentylthioisothiazole, followed by adding thereto 2.4 g (0.022 mole) of hydrogen peroxide, and the resulting mixture was heated from room temperature to 80° C. with stirring. The stirring was continued for 2 hours, after which water was added and the crystals precipitated were collected by filtration, washed with water and then dried. Recrystallization from ether gave 2.0 g (yield 64%) of white crystals having a melting point of 63–64° C.

Example 12

Synthesis of 3-difluoromethoxy-4-cyano-5-s-butylsulfonyl-isothiazole

In 7 ml of acetic acid was dissolved 2.64 g (0.01 mole) of 3-difluoromethoxy-4-cyano-5-s-butylthioisothiazole, followed by adding thereto 2.75 g (0,025 mole) of 31% hydrogen peroxide, and the resulting mixture was heated to 80° C. and subjected to reaction with stirring for 1 hour. Water was added to the reaction mixture and the desired compound was extracted with ethyl acetate, washed with water, and then dried. Thereafter, the ethyl acetate was distilled off under reduced pressure to obtain crude crystals. The crude crystals were recrystallized from n-hexane to obtain 2.1 g (yield 70%) of white crystals having a melting point of 42–43° C.

Example 13

Synthesis of 3-propargyloxy-4-cyano-5-difluoromethylsulfonylisothiazole

In 30 ml of dioxane was dissolved 2.4 g (0.01 mole) of 3-propargyloxy-4-cyano-5-methylsulfonylisothiazole, after which 20 g of sodium hydrosulfide (NaSH) and 10 ml of water were added with stirring at room temperature and the stirring was continued for 20 minutes. Then, 20 ml of 30% KOH was added and difluorodichloromethane was bubbled into the resulting mixture with stirring. After the bubbling for 30 minutes, water was added to the reaction mixture and the reaction product was extracted with ethyl acetate. The extract was washed with water, dried and then concentrated under reduced pressure to obtain 2.0 g of 3-propargyloxy-4-cyano- 5-difluoromethylthio-isothiazole. This compound was dissolved in 15 ml of acetic acid, followed by adding thereto 4.0 g of hydrogen peroxide, and the resulting mixture was stirred with heating at 70° C. for 5 hours. Water was added to the mixture and the crystals precipitated were collected by filtration and washed with water. Recrystallization from ether gave 1.5 g (yield 64%) of white crystals having a melting point of 83–84° C.

$^1$HNMR (CDCl$_3$) σ;2.64 (1H, m), 5.12 (2H, d), 6.29–6.64 (1H, m),

The compounds of the general formula (I) are effective in controlling various plant diseases and wood-rotting fungi. The plant diseases include, for example, rice blast (*Pyricularia oryzae*), cucumber downy mildew (*Pseudoperonospora cubensis*), tomato late blight (*Phytophthora infestans*), late blight or Phytophthora rots of other host plants, grape brown spot (*Cladosporium cladosporioides*), rice seedling blight (*Trichoderma viride*), apple alternaria leaf spot (*Alternaria mali*), sweet potato stem rot (*Fusarium oxysporum*), sweet potato rot (*Rhizopus nigricans*), onion black mold (*Aspergillus niger*), and rice "Bakanae" disease (*Gibberella fujikuroi*), powdery mildew of various host plants, such as powdery mildew of barley and wheat (*Erysiphe graminis*), that of cucumber (*Sphaerotheca fuliginea*), that of apple (*Podosphaera leucotricha*) and that of grape (*Uncinula necator*); wheat leaf rust (*Puccina recondita*); oats crown rust (*Puccina coronate*) and rust of other host plants. The wood-rotting fungi include, for example, brown rot (*Tyromyces palustris*), white rot (*Coriolus versicolor*) and dry rot (*Selupula lacrymas*).

For formulating the compound of the present invention into a form of composition, the compound and, optionally an adjuvant, are blended with a suitable inert carrier in a proper proportion and prepared into a suitable preparation form such as a solution, a suspension, an oil formulation, an emulsifiable concentrate, dust, granules, a wettable powder, tablets, pellets, a paste or an aerosol through dissolution, dispersion, suspension, mixing, impregnation, adsorption or sticking. As the inert carrier, any of solid, liquid and gaseous carriers may be used. As the solid carrier, there can be exemplified soybean flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica, synthetic silicates, and synthetic, high-dispersion silicic acid), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, ammonium chloride and urea), and compost. These carriers may be used alone or as a mixture thereof.

The liquid carrier is that which itself has solubility or which is without such solubility but is capable of dispersing an active ingredient with the aid of an adjuvant. The following are examples of the liquid carrier and can be used alone or as a mixture thereof. Water; alcohols such as methanol, ethanol, isopropanol and ethylene glycol; ketones such as acetone, methyl ethyl ketone and cyclohexanone; ethers such as ethyl ether, dioxane, tetrahydrofuran and Cellosolve; aliphatic hydrocarbons such as gasoline and kerosene; aromatic hydrocarbons such as benzene, toluene, xylene, solvent naphtha, cyclohexanone and methylnaphthalene; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylforamide, diethylformamide and dimethylacetamide; nitriles such as acetonitrile; and dimethyl sulfoxide.

The gaseous carrier includes, for example, Freon, butane gas, dimethyl ether, carbonic acid gas and LPG (liquefied petroleum gas).

As the adjuvant, the following adjuvants can be exemplified. They are used depending upon purposes and used alone or in combination in some cases, or need not to be used at all. To emulsify, disperse, dissolve and/or wet an active ingredient, there can be used surfactants such as polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylaryl sorbitan monolaurates, alkylbenzenesulfonates, alkylnaphthalenesulfonates, lignin-sulfonates and higher alcohol sulfate esters.

Further, to stabilize the dispersion of an active ingredient, tackify it and/or bind it, there may be used adjuvants such as casein, gelatin, starch, alginic acid, CMC, gum arabic, agar, polyvinyl alcohols, turpentine, bran oil, bentonite, lignin and sulfite liquor.

To improve the flowability of a solid product, there may be used adjuvants such as waxes, stearic acid and alkyl phosphates.

Adjuvants such as naphthalenesulfonic acid condensation products and phosphates may be used as a peptizer for dispersible products.

Defoaming agents such as silicon oils may also be added.

When the compound of the present invention is applied as an agricultural and horticultural fungicide, the applying dosage of the active ingredient, i.e., the compound is varied depending upon various factors such as purpose, a plant to be treated, a growth state of the plant, outbreak of fungi, weather, environmental conditions, a preparation form, an application method, an application site and an application time. It is properly chosen in the range of 0.1 g to 1 kg per 10 ares.

The content of the active ingredient may be varied as required. In dusts or granules, the content is usually 0.5 to 20%. In emulsifiable concentrates, suspensions or wettable powders, the content is 0.1 to 90%.

The agricultural and horticultural fungicide containing the compound of the present invention as an active ingredient may be used in admixture with other agricultural and horticultural fungicides in order to expand both spectrum of controllable diseases and the period of time when effective applications are possible or to reduce the dosage. The agricultural and horticultural fungicide containing the compound of the present invention as an active ingredient has a marked fungicidal effect on the above-exemplified diseases which damage paddy field crops, upland crops, fruit trees, vegetables, other crops, flowers and ornamental plants, and the like. Therefore, the desired effects of the agricultural and horticultural fungicide of the present invention can be obtained by applying the fungicide to the paddy field water, stalks and leaves of fruit trees, vegetables, other crops, flowers and ornamental plants, soil, etc., at a season at which the diseases are expected to occur, before their occurrence or at the time when their occurrence is confirmed.

A wood preservative containing the compound of the present invention as an active ingredient can be used, for example, in wood products such as plywoods, sawn lumber, particle boards and fiber-boards.

As such a wood preservative, the compound of the present invention can be used for controlling wood-rotting fungi by applying the compound to, in particular, building materials by surface treatment (e.g. coating, spraying or immersion) of a wood part, etc. with the undiluted compound or a dilution of the compound with water or the like, or injection of the undiluted compound or the dilution into wood, etc. under pressure or in a vacuum, or addition of the compound to an adhesive for plywood.

A preparation to be thus applied is varied depending upon a preparation form, an application time, an application site, an application method, wood-rotting fungi to be controlled, a degree of damage, etc. It is usually sufficient that a preparation containing the active ingredient in an amount of 0.1 g to 40 g per $m^3$ of wood is applied.

When the compound of the present invention is used as a wood preservative, it may be used in admixture with other wood preservatives, insecticides, acaricides, termite controlling agents, fungicides and synergists. The other wood preservatives include, for example, 3-iodo- 2-propynylbutyl carbamate, 3-iodopropargyl and zinc naphthenate. The termite controlling agents include, for example, Chlorpyrifos, Phoxim, Fenitrothion, Permethrin, Cypermethrin and Fenvalerate.

Formulation examples for the compound of the general formula (I) are described below but they should not be construed as limiting the scope of the invention. In the formulation examples, parts are all by weight.

Formulation Example 1

| | |
|---|---|
| Each compound of the invention | 50 parts |
| Xylene | 40 parts |
| Mixture of polyoxyethylene nonylphenyl ether and alkyl-benzenesulfonic acid | 10 parts |

An emulsifiable concentrate was prepared by mixing uniformly the above ingredients to effect dissociation.

Formulation Example 2

| | |
|---|---|
| Each compound of the invention | 0.5 part |
| Xylene | 0.8 part |
| Illuminating kerosine | 98.7 parts |

An oil formulation was prepared by mixing uniformly the above ingredients to effect dissociation.

Formulation Example 3

| | |
|---|---|
| Each compound of the invention | 3 parts |
| Clay powder | 82 parts |
| Diatomaceous earth powder | 15 parts |

A dust was prepared by mixing uniformly and grinding the above ingredients.

Formulation Example 4

| | |
|---|---|
| Each compound of the invention | 5 parts |
| Mixed powder of bentonite and clay | 90 parts |
| Calcium stearate | 1 part |

Granules were prepared by mixing the above ingredients uniformly, and kneading the resulting mixture together with a suitable amount of water, followed by granulation and drying.

Formulation Example 5

| | |
|---|---|
| Each compound of the invention | 20 parts |
| Mixture of kaolin and synthetic, high-dispersion silicic acid | 75 parts |
| Mixture of polyoxyethylene | 5 parts |

-continued nonylphenyl ether and calcium
alkylbenzenesulfonate                                    5

A wettable powder was prepared by mixing uniformly and grinding the above ingredients.

Next, the effects of the preparations of the present invention are explained with reference to the following test examples, which should not be construed as limiting the scope of the invention.

Test Example 1

Each preparation to be tested was added to malt extract agar medium to adjust the concentration to 50 ppm, and the resulting mixture was dispensed into Petri dishes. As an inoculum, a prepared mycerial tuft of each test fungus was punched out together with agar by means of a 4-mm-diameter cork borer and inoculated on medium. The incubation temperature was adjusted to 28±2° C. (or 18±2° C. in the case of *Selupula lacrymas*).

The diameter of mycerial tuft was measured 2 to 10 days after the inoculation, and the inhibition rate of hypha growth (the following equation) was measured.

Growth inhibition rate (%) =

$$\frac{\left[\begin{array}{c}\text{Diameter of}\\\text{untreated}\\\text{myceial tuft}\end{array}\right] - \left[\begin{array}{c}\text{Diameter of}\\\text{mycerial tuft in}\\\text{experimental plot}\end{array}\right]}{\left[\begin{array}{c}\text{Diameter of untreated}\\\text{mycerrial tuft}\end{array}\right]} \times 100$$

The controlling effect was evaluated according to the following criterion. The results obtained are shown in Table 2.

| Growth inhibition rate (%) | Effect |
|---|---|
| 100 | A |
| 99–85 | B |
| 84–55 | C |
| 54 or less | D |

TABLE 2

| Compound No. | Controlling effect | | | | | | | | | |
|---|---|---|---|---|---|---|---|---|---|---|
| | TYP | COV | SEL | CLC | TRV | ALM | FUO | ASN | CHG | RHS |
| 1 | C | B | B | C | B | C | C | C | B | B |
| 2 | C | B | C | C | B | C | C | C | B | B |
| 11 | B | B | C | C | B | C | B | C | B | B |
| 15 | A | A | A | A | A | A | A | A | A | A |
| 16 | A | B | A | A | A | A | B | A | A | A |
| 17 | A | B | A | A | A | A | A | A | A | A |
| 18 | A | A | A | A | A | B | B | A | A | A |
| 20 | A | A | A | A | A | A | A | A | A | A |
| 22 | A | A | A | A | B | B | B | B | C | B |
| 24 | A | A | A | A | A | A | B | A | C | B |
| 28 | A | A | A | B | A | A | A | B | B | A |
| 29 | A | A | B | B | A | B | B | B | A | A |
| 30 | A | A | B | B | A | B | B | B | A | A |
| 34 | A | A | B | B | A | A | A | A | A | A |
| 43 | A | A | A | A | B | B | B | B | B | A |
| 50 | A | A | A | A | A | A | A | A | A | A |
| 57 | A | A | A | A | B | B | A | B | B | B |
| 59 | A | A | A | A | A | A | A | A | A | A |
| 73 | A | A | A | B | B | B | A | B | A | A |
| 77 | B | A | A | B | A | B | B | B | A | A |
| 81 | A | A | A | A | A | A | A | A | A | A |
| 82 | A | A | A | A | A | A | A | A | A | A |
| 89 | A | A | A | A | A | A | A | A | A | A |
| 93 | A | A | A | A | A | A | A | A | A | A |
| 94 | A | A | A | A | A | A | A | A | A | A |
| 96 | A | A | A | A | A | A | A | A | A | A |
| 97 | A | A | A | B | A | A | A | B | A | A |
| 100 | A | A | A | A | A | A | A | A | A | A |
| 109 | A | A | A | A | A | A | A | A | A | A |
| 111 | A | B | B | A | A | A | B | A | A | A |
| 113 | A | A | A | A | A | A | A | A | A | A |
| 117 | B | A | A | B | A | B | B | A | A | A |
| 119 | B | A | A | A | A | B | B | B | A | A |
| 140 | A | A | A | A | A | A | A | A | A | A |
| 144 | A | A | A | A | A | A | A | A | A | A |
| 148 | A | A | A | A | A | A | A | A | A | A |

Test fungi
Basidiomycetes;
TYP (*Tyromyces palustris*)
COV (*Coriolus versicolor*)

TABLE 2-continued

| Compound | Controlling effect | | | | | | | | |
|---|---|---|---|---|---|---|---|---|---|
| No. | TYP | COV | SEL | CLC | TRV | ALM | FUO | ASN | CHG | RHS |

SEL (*Serpula lacrymans*)
Deuteromycotina;
CLC (*Cladosporium cladosporioides*)
TRV (*Trichoderma viride*)
ALM (*Alternaria mali*)
Ascomycetes;
FUO (*Fusarium oxysporum*)
ASN (*Aspergillus niger*)
CEG (*Chaetomium globosum*)
Zygomycetes;
RHS (*Rhizopus nigricans*)

Test Example 2

Unhulled rice infected by "Bakanae" disease fungus (Gibberella fujikuroi) was immersed in each preparation to be tested which had a concentration of 200 ppm, at 25° C. for 24 hours. Water was lightly drained off from the unhulled rice, after which the unhulled rice was placed on Fusarium selective medium. The test was carried out with groups of 5 grains each. The growth rate of hyphae was investigated 5 to 7 days after the placement, and the index described below was calculated and then expressed in terms of controlling degree rating. The results obtained are shown in Table 3.

| Hypha growth index | | Rating |
|---|---|---|
| No growth | 0; | A |
| Slight growth | 0.1; | B |
| Hyphae grew on less than 1/3 of the unhulled-rice surface | 0.5; | C |
| Hyphae grew on 1/3 of the unhulled-rice surface | 1.0; | |
| Hyphae grew on 2/3 of the unhulled-rice surface | 2.0; | D |
| Hyphae grew on the whole unhulled-rice surface | 3.0; | |

TABLE 3

| Compound No. | Controlling effect | Compound No. | Controlling effect | Compound No. | Controlling effect |
|---|---|---|---|---|---|
| 1 | C | 30 | A | 94 | A |
| 2 | C | 34 | A | 96 | A |
| 11 | B | 43 | A | 97 | A |
| 15 | A | 50 | B | 100 | A |
| 16 | A | 57 | A | 109 | C |
| 17 | B | 59 | C | 111 | A |
| 18 | A | 73 | A | 113 | A |
| 20 | A | 77 | A | 117 | A |
| 22 | A | 81 | A | 119 | B |
| 24 | A | 82 | A | Reference compound | C |
| 28 | B | 89 | A | | |
| 29 | A | 93 | A | | |

Reference compound: the compound described in French Patent No. 1,555,414.

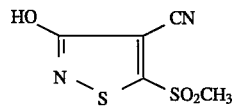

Test Example 3

Controlling effect on cucumber Downy mildew

Potted cucumber plants at the 2 leaf stage were sprayed with a 200 ppm liquid chemical containing each compound of the present invention as active ingredient. After 24 hours, they were inoculated with a suspension of zoospores of Downy mildew fungus (*Pseudoperonospora cubensis*) by spraying.

After the inoculation, the plants were placed in a moist chamber at 25° C. for 1 day and then a greenhouse for 6 days to cause the disease sufficiently. Thereafter, the degree of occurrence of the disease in each leaf was investigated by comparison with that on the untreated plot, and the effect was judged according to the following criterion.

| Effect | Controlling degree (%) |
|---|---|
| A | 100–95 |
| B | 94–80 |
| C | 79–60 |
| D | 59–0 |

The results obtained are shown in the "Pc" column in Table 4.

Test Example 4

Controlling effect on tomato late blight

Potted tomato plants at the 4 leaf stage were sprayed with a 200 ppm liquid chemical containing each compound of the present invention as active ingredient. After 24 hours, they were inoculated with a suspension of zoospores of late blight fungus (Phytophthora infestants) by spraying. The plants were placed in a moist chamber at 25° C. for 1 day and then a greenhouse for 6 days to cause the disease sufficiently. Thereafter, the degree of occurrence of the disease in each leaf was investigated and then compared with that on the untreated plot, whereby the effect was judged according to the same criterion as described in Test Example 3.

The results obtained are shown in the "Pi" column in Table 4.

Test Example 5

Controlling effect on rice blast by spraying

Potted rice plants at the 5 leaf stage were sufficiently sprayed with a 200 ppm liquid chemical containing each compound of the present invention as active ingredient. After air-drying, the plants were inoculated with a suspension of conidiospore of blast fungus (*Pyricularia oryzae*) by spraying.

After the inoculation, the plants were placed in a moist chamber at 20° C. for 1 day and then a greenhouse for 6 days to cause the disease sufficiently. Then, lesions in each leaf were counted and then compared with those on the untreated plot, whereby the effect was judged according to the same criterion as described in Test Example 3.

The results obtained are shown in the "Ps" column in Table 4.

Test Example 6

Controlling effect (curing effect) on cucumber gray mold

The cotyledons of potted cucumber plants at the 1 leaf stage were cut off and each of them was inoculated with a mycelial tuft of gray mold fungus (*Botrytis cinerea*) cultured on PSA medium. After having been placed in a moist chamber at 15° C. for 24 hours, the cotyledons were immersed in a 200 ppm liquid chemical containing each compound of the present invention as active ingredient.

Then, the cotyledons were placed in a moist chamber at 15° C. for 3 days to cause the disease sufficiently, after which the diameter of lesions was measured and then compared with that on the untreated plot, whereby the effect was judged according to the same criterion as described in Test Example 3.

The results obtained are shown in the "Bc" column in Table 4.

TABLE 4

| Compound No. | Controlling effect | | | |
|---|---|---|---|---|
| | Pc | Pi | Ps | Bc |
| 1 | C | C | B | D |
| 5 | C | B | C | D |
| 15 | A | A | A | C |
| 16 | A | A | B | C |
| 20 | A | A | A | C |
| 21 | A | A | A | C |
| 22 | B | A | A | D |
| 23 | A | A | A | C |
| 24 | A | A | A | D |
| 25 | A | A | B | C |
| 27 | B | A | A | D |
| 35 | A | A | A | D |
| 37 | A | A | A | D |
| 38 | A | A | A | C |
| 50 | A | B | B | D |
| 52 | A | A | B | C |
| 58 | A | A | B | D |
| 82 | A | A | A | C |
| 89 | B | A | A | C |
| 90 | A | A | A | C |
| 93 | A | A | A | C |
| 104 | B | A | A | C |
| 120 | A | A | A | C |
| 140 | A | A | A | A |
| 141 | A | A | A | B |
| 144 | A | A | A | A |
| 145 | A | A | A | D |
| 148 | B | A | A | C |

Pc: cucumber downy mildew
Pi: tomato late blight
Ps: rice blast
Bc: cucumber gray mold The compounds of the present invention have an excellent controlling effect on wood-rotting fungi, plant diseases, etc. and are useful as wood preservatives and agricultural and horticultural fungicides.

What is claimed is:

1. An isothiazole derivative represented by the formula (I):

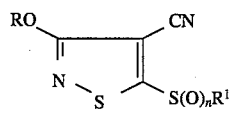

wherein R is a hydrogen atom; a $C_{1-12}$ alkyl group; a $C_{2-7}$ alkenyl group; a $C_{3-7}$ alkynyl group; a $C_{3-7}$ cycloalkyl group; a substituted alkyl group having as the substituent(s) 1 or 2 atoms or groups selected from the group consisting of halogen atoms but excluding perfluoro and perchloro, $C_{1-6}$ alkoxy groups, cyano group, $C_{2-7}$ alkoxycarbonyl groups, phenyl group, phenoxy group, phenoxyphenyl group, trialkylsilyl groups, $C_{2-7}$ alkylcarbonyl groups, and groups represented by the formula —A—N($R^2$)$_2$ (wherein $R^2$ is a $C_{1-6}$ alkyl group or forms a $C_{2-6}$ alkylene group by binding of two $R^2$'s to each other, and A is a carbonyl group or a $C_{2-6}$ alkylene group) triazolyl alkyl, benzimidazolyl alkyl, oxazolyl alkyl or pyridyl alkyl which may be substituted with a chlorine atom(s) or a $C_{1-6}$ alkyl group(s); or a substituted $C_{2-7}$ alkenyl group having a halogen atom or a phenyl group as the substituent, $R^1$ is a $C_{1-12}$ alkyl group; a $C_{1-4}$ haloalkyl group; a $C_{2-7}$ alkenyl group; a $C_{3-7}$ alkynyl group; a $C_{3-7}$ cycloalkyl group; a heteroarylalkyl group; a substituted $C_{1-6}$ alkyl group having as the substitutent a group selected from the group consisting of phenyl group, substituted phenoxy groups having 1 or 2 halogen atoms as the substituent(s), and phenoxyphenyl group; or an aryl group, $R^1$ being an aryl group in the case of R being a hydrogen atom, and n is an integer of 1 or 2.

2. An isothiazole derivative according to claim 1, wherein R is $C_1$–$C_4$ alkyl group, $C_3$–$C_5$ alkenyl group, $C_3$–$C_5$ alkynyl group or $C_1$–$C_4$ haloalkyl group, $R^1$ is $C_1$–$C_4$ alkyl group, $C_3$–$C_5$ alkenyl group, $C_3$–$C_5$ alkynyl group or $C_1$–$C_4$ haloalkyl group.

3. An isothiazole derivtive according to claim 1, wherein R is $C_1$–$C_3$ alkyl group or difluoromethyl group, $R_1$ is methyl group or difluoromethyl group.

4. A process for producing an isothiazole derivative represented by the formula (I):

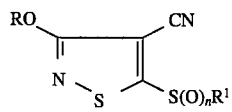

(wherein R is a hydrogen atom; a $C_{1-12}$ alkyl group; a $C_{2-7}$ alkenyl group; a $C_{3-7}$ alkynyl group; a $C_{3-7}$ cycloalkyl group; a substituted alkyl group having as the substituent(s) 1 or 2 atoms or groups selected from the group consisting of halogen atoms but excluding perfluoro and perchloro, $C_{1-6}$ alkoxy groups, cyano group, $C_{2-7}$ alkoxycarbonyl groups, phenyl group, phenoxy group, phenoxyphenyl group, trialkylsilyl groups, $C_{2-7}$ alkylcarbonyl groups, and groups represented by the formula —A—N($R^2$)$_2$ (wherein $R^2$ is a $C_{1-6}$ alkyl group or forms a $C_{2-6}$ alkylene group by binding of two $R^2$'s to each other, and A is a carbonly group or a $C_{2-6}$ alkylene group) tirazolyl alkyl, benzimidazolyl alkyl, oxazolyl alkyl or pyridyl alkyl which may be substituted with a chlorine atom(s) or a $C_{1-6}$ alkyl group(s); or a substituted $C_{2-7}$ alkenyl group having a halogen atom or a phenyl group as the substituent, $R^1$ is a $C_{1-12}$ alkyl group; a $C_{1-4}$ haloalkyl group; a $C_{2-7}$ alkenyl group; a $C_{3-7}$ alkynyl group; a $C_{3-7}$ cycloalkyl group; a heteroarylalkyl group; a substituted $C_{1-6}$ alkyl group having as the substitutent a group selected from the group consisting of phenyl group, substituted phenoxy groups having 1 or 2 halogen atoms as the substituent(s), and phenoxyphenyl group; or an aryl group, $R^1$ being an aryl group in the case of R being a hydrogen atom, and n is an integer of 1 or 2) which comprises oxidizing with an oxidizing agent, a compound represented by the formula (II):

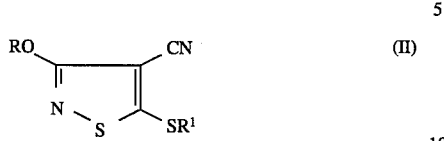
(II)

(wherein R and $R^1$ are as defined above).

5. A process for producing an isothiazole derivative represented by the formula (Ib):

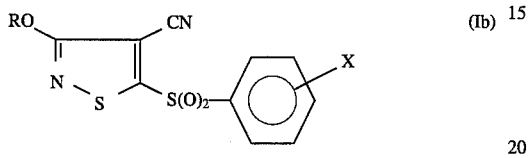
(Ib)

(wherein R is a hydrogen atom; a $C_{1-12}$ alkyl group; a $C_{2-7}$ alkenyl group; a $C_{3-7}$ alkynyl group; a $C_{3-7}$ cycloalkyl group; a substituted alkyl group having as the substituent(s) 1 or 2 atoms or groups selected from the group consisting of halogen atoms but excluding perfluoro and perchloro, $C_{1-6}$ alkoxy groups, cyano group, $C_{2-7}$ alkoxycarbonyl groups, phenyl group, phenoxy group, phenoxyphenyl group, trialkylsilyl groups, $C_{2-7}$ alkylcarbonyl groups, and groups represented by the formula $-A-N(R^2)_2$ (wherein $R^2$ is a $C_{1-6}$ alkyl group or forms a $C_{2-6}$ alkylene group by binding of two $R^2$'s to each other, and A is a carbonly group or a $C_{2-6}$ alkylene group) tirazolyl alkyl, benzimidazolyl alkyl, oxazolyl alkyl or pyridyl alkyl which may be substituted with a chlorine atom(s) or a $C_{1-6}$ alkyl group(s); or a substituted $C_{2-7}$ alkenyl group having a halogen atom or a phenyl group as the substituent, and X is a halogen atom, a $C_{1-6}$ alkyl group, a $C_{1-6}$ alkoxy group, a hydroxyl group, a nitro group, an amino group or a $C_{2-7}$ alkoxycarbonyl group) which comprises reacting a compound represented by the general formula (Ia):

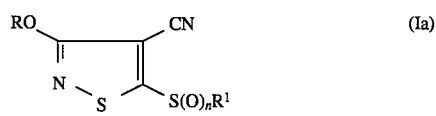
(Ia)

(wherein R is a defined above, $R_3$ is a $C_{1-6}$ alkyl group, and n is an integer of 1 or 2) with a compound of the general formula (III):

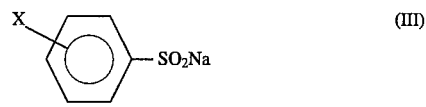
(III)

(wherein X is a defined above).

* * * * *

UNITED STATES PATENT AND TRADEMARK OFFICE
CERTIFICATE OF CORRECTION

PATENT NO.   :   5,484,934

DATED        :   January 16, 1996

INVENTOR(S)  :   IKEDA et al.

It is certified that error appears in the above-identified patent and that said Letters Patent is hereby corrected as shown below:

On title page,
Item [22]: delete "18" and replace --28-- therefor.

Signed and Sealed this

Ninth Day of July, 1996

Attest:

BRUCE LEHMAN

Attesting Officer

Commissioner of Patents and Trademarks